United States Patent [19]

Förster et al.

[11] Patent Number: 4,599,106
[45] Date of Patent: Jul. 8, 1986

[54] SUBSTITUTED ALKANETHIOCARBOXYLIC ACID DERIVATIVES AND HERBICIDAL USE THEREOF

[75] Inventors: Heinz Förster, Wuppertal; Ludwig Eue, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 736,748

[22] Filed: May 22, 1985

Related U.S. Application Data

[62] Division of Ser. No. 575,963, Feb. 1, 1984.

Foreign Application Priority Data

Feb. 8, 1983 [DE] Fed. Rep. of Germany ....... 3304204

[51] Int. Cl.$^4$ .................... A01N 37/00; C07C 153/11
[52] U.S. Cl. ...................... 71/100; 558/234; 568/12; 546/302
[58] Field of Search ................ 260/455 R; 71/100

[56] References Cited

U.S. PATENT DOCUMENTS 3,830,829 8/1974 Olin .......................... 260/455 R
3,954,442 5/1976 Becker et al. .............. 260/455 R

FOREIGN PATENT DOCUMENTS 0002204 6/1979 European Pat. Off. ........ 260/455 R
1939010 7/1970 Fed. Rep. of Germany ... 260/455 R
2758002 7/1979 Fed. Rep. of Germany ... 260/455 R

*Primary Examiner*—Henry R. Jiles
*Assistant Examiner*—Robert C. Whittenbaugh
*Attorney, Agent, or Firm*—Sprung Horn Kramer & Woods

[57] ABSTRACT

A substituted alkanethiocarboxylic acid derivative of the formula

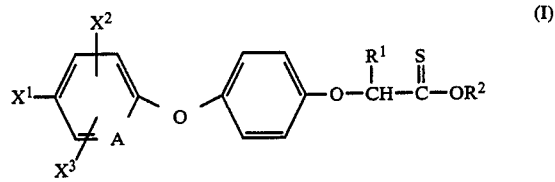

in which
A represents a CH grouping,
$X^1$ represents hydrogen, trifluoromethyl or chlorine,
$X^2$ and $X^3$ independently of one another represent hydrogen, trifluoromethyl or chlorine,
$R^1$ represents hydrogen or methyl and
$R^2$ represents hydrogen or optionally substituted radicals from the series comprising alkyl, alkenyl, alkinyl, aryl, aralkyl, aralkoxyalkyl and cycloalkyl and its use in a herbicidal composition for combating weeds.

15 Claims, No Drawings

SUBSTITUTED ALKANETHIOCARBOXYLIC ACID DERIVATIVES AND HERBICIDAL USE THEREOF

This is a division, of application Ser. No. 575,963, filed Feb. 1, 1984, now pending.

The invention relates to new substituted alkanethiocarboxylic acid derivatives, a process for their preparation and their use as herbicides.

It has already been disclosed that numerous phenoxypropionic acid derivatives have herbicidal properties (compare DE-OS (German Published Specification) 2,223,894). Thus, for example, methyl 2-[4-(2,4-dichloro-phenoxy)-phenoxy]-propionate can be used for combating weeds. However, the action of this substance is not always satisfactory, especially against some grasses and when low amounts are applied.

New substituted alkanethiocarboxylic acid derivatives of the formula

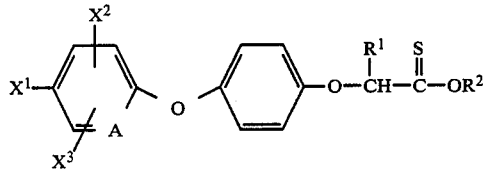

in which
A represents nitrogen or a CH grouping,
$X^1$ represents hydrogen, trifluoromethyl or chlorine,
$X^2$ and $X^3$ independently of one another represent hydrogen, trifluoromethyl or chlorine,
$R^1$ represents hydrogen or methyl and
$R^2$ represents hydrogen or optionally substituted radicals from the series comprising alkyl, alkenyl, alkinyl, aryl, aralkyl, aralkoxyalkyl and cycloalkyl,
have now been found.

Those substituted alkanethiocarboxylic acid derivatives of the formula (I) in which $R^1$ represents methyl contain an asymmetric carbon atom in the side chain and can therefore exist in two enantiomeric forms. The invention relates to particular racemates and to the R- and S-enantiomers.

It has furthermore been found that the substituted alkanethiocarboxylic acid derivatives of the formula (I) are obtained when phenoxyalkanecarboxylic acid derivatives of the formula

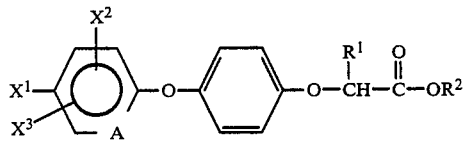

in which
A, $X^1$, $X^2$, $X^3$, $R^1$ and $R^2$ have the above-mentioned meaning,
are reacted with sulphurizing agents, if appropriate in the presence of a diluent.

Finally, it has been found that new substituted alkanethiocarboxylic acid derivatives of the formula (I) are distinguished by an outstanding herbicidal activity.

Surprisingly, the substituted alkanethiocarboxylic acid derivatives of the formula (I) according to the invention have better herbicidal properties than methyl 4-[4-(2,4-dichlorophenoxy)-phenoxy]-propionate, which is known from the prior art and is a highly effective and structurally similar active compound of the same type of action. Some graminaceous weeds which particularly occur in rice and are not affected by methyl 4-[4-(2,4-dichlorophenoxy)-phenoxy]-propionate can above all be effectively combated with the aid of the active compounds of the formula (I) according to the invention.

The substituted alkanethiocarboxylic acid derivatives according to the invention are defined unambiguously by the formula (I).

Preferably, in this formula
A represents nitrogen or a —CH-grouping,
$X^1$ represents hydrogen, trifluoromethyl or chlorine,
$X^2$ represents hydrogen, trifluoromethyl or chlorine,
$X^3$ represents hydrogen, trifluoromethyl or chlorine,
$R^1$ represents hydrogen or methyl and
$R^2$ represents hydrogen, or represents alkyl which has 1 to 6 carbon atoms and is optionally substituted by hydroxyl, halogen, such as fluorine, chlorine or bromine, $C_1$-$C_4$-alkoxy, $C_1$-$C_4$-alkylthio, $C_3$-$C_6$-cycloalkyl, amino, alkylamino with 1 to 4 carbon atoms, dialkylamino with 1 to 4 carbon atoms per alkyl radical and/or saturated 5-membered or 6-membered heterocyclic radicals which are bonded via nitrogen and contain up to 3 nitrogen and/or oxygen atoms, or represents alkenyl which is optionally substituted by fluorine, chlorine, bromine and/or iodine, or represents alkinyl which is optionally substituted by fluorine, chlorine, bromine and/or iodine, or represents phenyl which is optionally substituted by halogen, $C_1$-$C_4$-alkyl, $C_1$-$C_4$-alkylthio, $C_1$-$C_4$-alkoxy, cyano and/or nitro, or represents benzyl which is optionally substituted by halogen, $C_1$-$C_4$-alkyl, $C_1$-$C_4$-alkylthio, $C_1$-$C_4$-alkoxy, cyano and/or nitro, or represents phenylethyl which is optionally substituted in the phenyl part by halogen, $C_1$-$C_4$-alkyl, $C_1$-$C_4$-alkylthio, $C_1$-$C_4$-alkoxy, cyano and/or nitro, or represents phenyl-($C_1$-$C_4$)-alkoxy-($C_1$-$C_4$)-alkyl which is optionally substituted in the phenyl part by halogen, $C_1$-$C_4$-alkyl, $C_1$-$C_4$-alkylthio, $C_1$-$C_4$-alkoxy, cyano and/or nitro, or represents cycloalkyl which has 3 to 6 carbon atoms and is optionally substituted by alkyl with 1 to 4 carbon atoms and/or halogen.

A particularly preferred group of compounds according to the invention are those substances of the formula (I) in which A represents a CH group, $X^1$ represents trifluoromethyl, $X^2$ and $X^3$ represent hydrogen or chlorine, $R^1$ represents methyl and $R^2$ represents methyl or ethyl.

A further group of particularly preferred compounds according to the invention are those substances of the formula (I) in which A represents nitrogen, $X^1$ represents chlorine or trifluoromethyl, $X^2$ represents hydrogen or chlorine, $X^3$ represents hydrogen, $R^1$ represents methyl and $R^2$ represents methyl or ethyl.

The compounds listed by way of their formulae in the following tables may be mentioned as further particularly preferred groups of compounds of the formula (I) according to the invention:

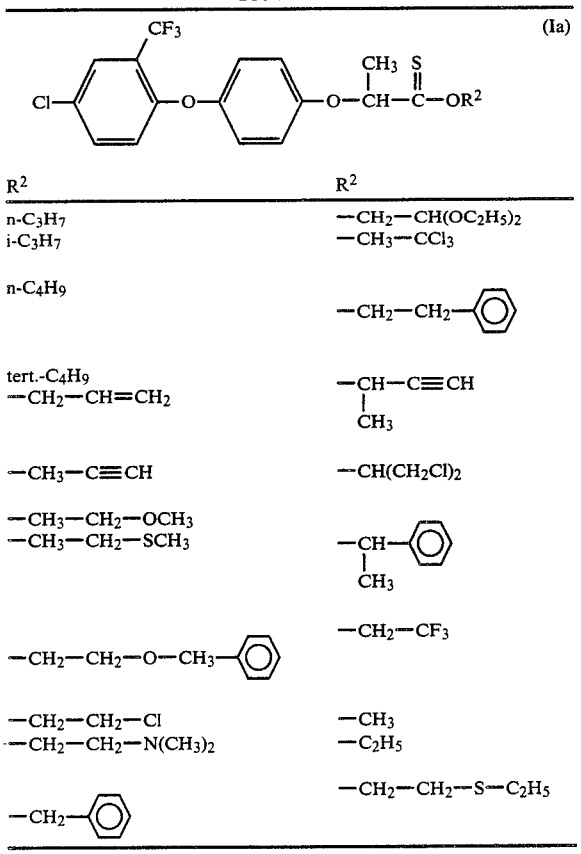
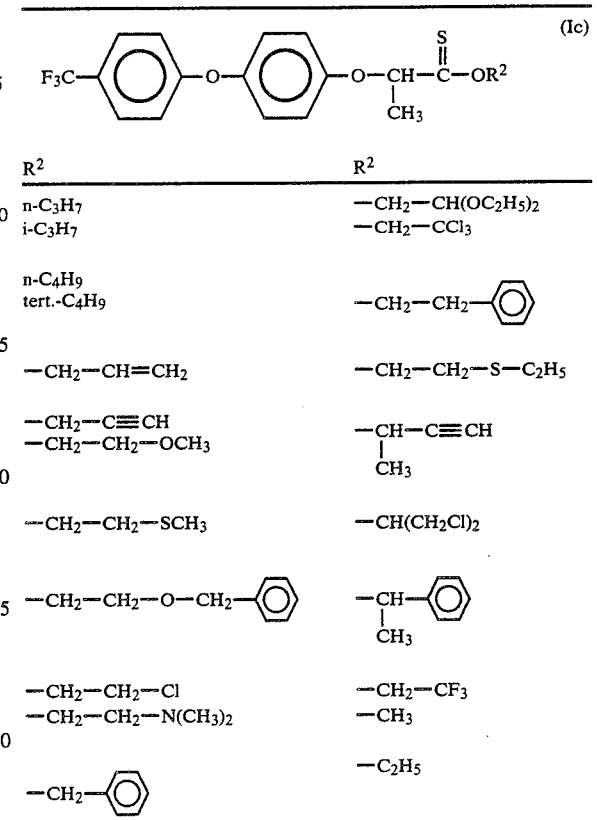
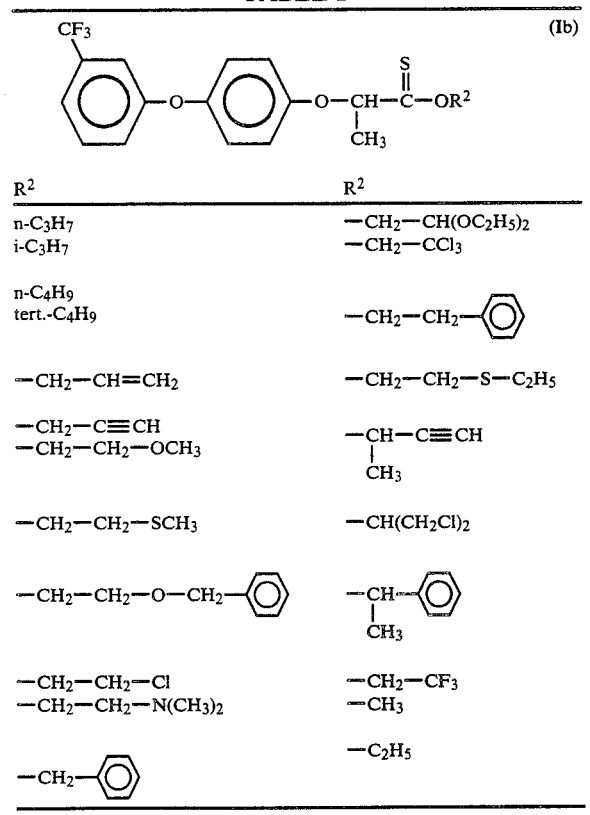
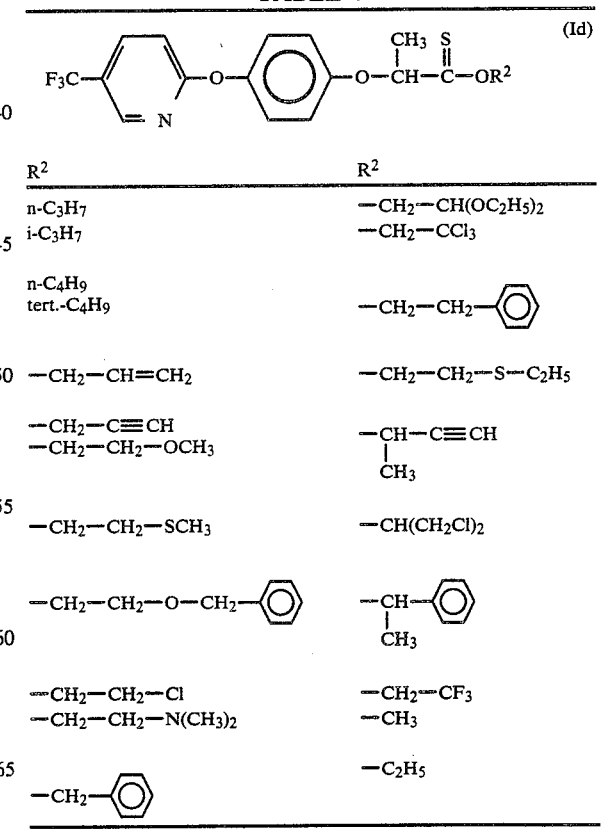

TABLE 5

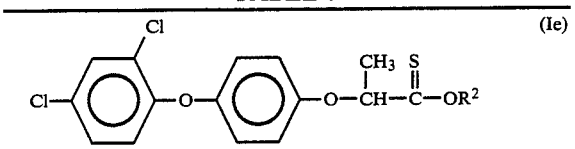
(Ie)

| $R^2$ | $R^2$ |
|---|---|
| n-C$_3$H$_7$ | —CH$_2$—CH(OC$_2$H$_5$)$_2$ |
| i-C$_3$H$_7$ | —CH$_2$—CCl$_3$ |
| n-C$_4$H$_9$ | |
| tert.-C$_4$H$_9$ | —CH$_2$—CH$_2$—C$_6$H$_5$ |
| —CH$_2$—CH=CH$_2$ | —CH$_2$—CH$_2$—S—C$_2$H$_5$ |
| —CH$_2$—C≡CH | —CH—C≡CH |
| —CH$_2$—CH$_2$—OCH$_3$ | $\quad$ CH$_3$ |
| —CH$_2$—CH$_2$—SCH$_3$ | —CH(CH$_2$Cl)$_2$ |
| —CH$_2$—CH$_2$—O—CH$_2$—C$_6$H$_5$ | —CH—C$_6$H$_5$ |
| | $\quad$ CH$_3$ |
| —CH$_2$—CH$_2$—Cl | —CH$_2$—CF$_3$ |
| —CH$_2$—CH$_2$—N(CH$_3$)$_2$ | —CH$_3$ |
| | —C$_2$H$_5$ |
| —CH$_2$—C$_6$H$_5$ | |

TABLE 6

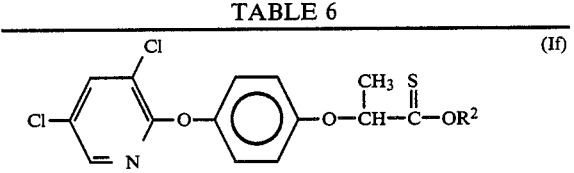
(If)

| $R^2$ | $R^2$ |
|---|---|
| n-C$_3$H$_7$ | —CH$_2$—CH(OC$_2$H$_5$)$_2$ |
| i-C$_3$H$_7$ | —CH$_2$—CCl$_3$ |
| n-C$_4$H$_9$ | |
| tert.-C$_4$H$_9$ | —CH$_2$—CH$_2$—C$_6$H$_5$ |
| —CH$_2$—CH=CH$_2$ | —CH$_2$—CH$_2$—S—C$_2$H$_5$ |
| —CH$_2$—C≡CH | —CH—C≡CH |
| —CH$_2$—CH$_2$—OCH$_3$ | $\quad$ CH$_3$ |
| —CH$_2$—CH$_2$—SCH$_3$ | —CH(CH$_2$Cl)$_2$ |
| —CH$_2$—CH$_2$—O—CH$_2$—C$_6$H$_5$ | —CH—C$_6$H$_5$ |
| | $\quad$ CH$_3$ |

TABLE 6-continued

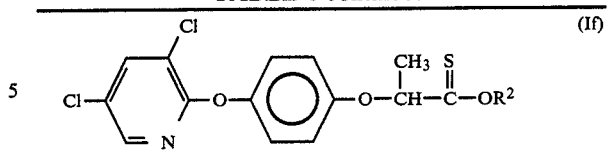
(If)

| $R^2$ | $R^2$ |
|---|---|
| —CH$_2$—CH$_2$—Cl | —CH$_2$—CF$_3$ |
| —CH$_2$—CH$_2$—N(CH$_3$)$_2$ | —CH$_3$ |
| | —C$_2$H$_5$ |
| —CH$_2$—C$_6$H$_5$ | |

TABLE 7

(Ig)

| $R^2$ | $R^2$ |
|---|---|
| n-C$_3$H$_7$ | —CH$_2$—CH(OC$_2$H$_5$)$_2$ |
| i-C$_3$H$_7$ | —CH$_2$—CCl$_3$ |
| n-C$_4$H$_9$ | |
| tert.-C$_4$H$_9$ | —CH$_2$—CH$_2$—C$_6$H$_5$ |
| —CH$_2$—CH=CH$_2$ | —CH$_2$—CH$_2$—S—C$_2$H$_5$ |
| —CH$_2$—C≡CH | —CH—C≡CH |
| —CH$_2$—CH$_2$—OCH$_3$ | $\quad$ CH$_3$ |
| —CH$_2$—CH$_2$—SCH$_3$ | —CH(CH$_2$Cl)$_2$ |
| —CH$_2$—CH$_2$—O—CH$_2$—C$_6$H$_5$ | —CH—C$_6$H$_5$ |
| | $\quad$ CH$_3$ |
| —CH$_2$—CH$_2$—Cl | —CH$_2$—CF$_3$ |
| —CH$_2$—CH$_2$—N(CH$_3$)$_2$ | —CH$_3$ |
| | —C$_2$H$_5$ |
| —CH$_2$—C$_6$H$_5$ | |

The R-enantiomers of the abovementioned compounds are also particularly preferred.

If ethyl 2-[4-(4-chloro-2-trifluoromethyl-phenoxy)-phenoxy]-propionate is used as the starting substance and 2,4-bis(4-methoxy-phenyl)-1,3,2,4-dicyclothiaphosphane-2,4-disulphide is used as the sulphurising agent, the course of the process according to the invention can be represented by the following equation:

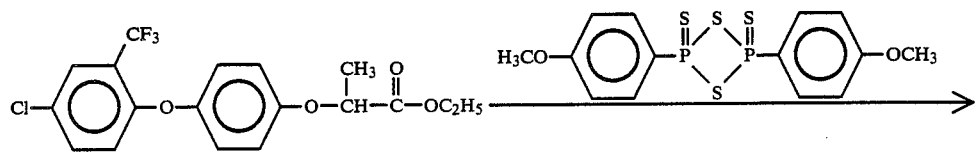

-continued

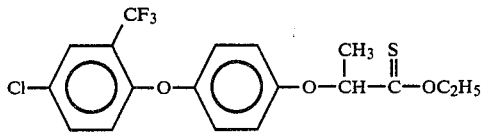

The phenoxyalkanecarboxylic acid derivatives required as starting substances in carrying out the process according to the invention are defined unambiguously by the formula (II). In this formula, A, $X^1$, $X^2$, $X^3$, $R^1$ and $R^2$ preferably have those meanings which have already been mentioned as preferred for these radicals in connection with the description of the substances of the formula (I) according to the invention.

Examples which may be mentioned of phenoxyalkanecarboxylic acid derivatives of the formula (II) are those substances which correspond to the alkanethiocarboxylic acid derivatives of the formula (I) listed in Tables 1 to 7.

The phenoxyalkanecarboxylic acid derivatives of the formula (II) are known, or they can be prepared in a simple manner by known methods (compare DE-OS (German Published Specification ) No. 3,219,789, DE-OS (German Published Specification) No. 3,221,214, DE-OS (German Published Specification) No. 3,219,821, Belgian patent specification No. 862,325, Belgian patent specification No. 868,875, EP-OS (European Published Specification ) No. 483, EP-OS (European Published Specification) No. 17,767, EP-OS (European Published Specification) No. 1,473, U.S. Pat. No. 4,301,295 and DE-OS (German Published Specification) No. 2,946,652).

Possible sulphurizing agents in carrying out the process according to the invention are all those reagents which are suitable for converting C=O groups into C=S groups. Phosphorous pentasulphide can preferably be used, if appropriate on carriers, such as, for example, magnesium oxide. 2,4-Bis(4-methoxyphenyl)-1,3,2,4-dicyclothiaphosphane 2,4-disulphide of the formula

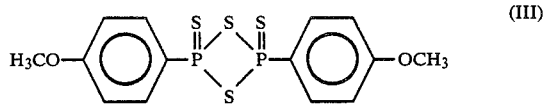

(III)

can furthermore preferably be used.

These sulphurizing agents are known, or they can be prepared in a simple manner by known processes (compare DE-OS (German Published Specification) No. 2,511,230, Bull. Soc. Chim. Belg. 1978, 87(3), 229-238 and Chem. Abstr. 89, 108 050 t).

To prepare the R- and S-enantiomers of those substituted alkanethiocarboxylic acid derivatives of the formula (I) in which $R^1$ represents methyl, the corresponding optically active phenoxyalkanecarboxylic acid derivatives of the formula

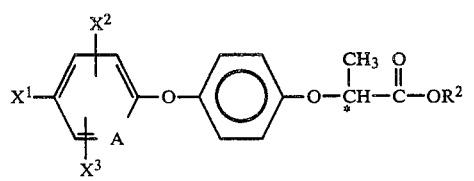

(IIa)

in which

A, $X^1$, $X^2$, $X^3$, and $R^2$ have the abovementioned meaning, are reacted with sulphurizing agents by the process according to the invention.

The optically active phenoxyalkanecarboxylic acid derivatives of the formula (IIa) are likewise known, or they can be prepared by known methods (compare the abovementioned literature). In formula (IIa), the asymetrically substituted carbon atom is marked by (*).

The process according to the invention for the preparation of the new substances of the formula (I) is preferably carried out using diluents. Possible diluents are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, chlorobenzene and o-dichlorobenzene, and ethers, such as dibutyl ether, glycol dimethyl ether and diglycol dimethyl ether, tetrahydrofuran and dioxane.

The reaction temperatures can be varied within a substantial range in the process according to the invention. In general, the reaction is in each case carried out at temperatures between 20° C. and 190° C., preferably between 110° and 160° C.

The process according to the invention is in general carried out under normal pressure. However, it is also possible to carry out the process under increased or reduced pressure.

In carrying out the process according to the invention, the starting substances are in general employed in approximately equimolar amounts. However, it is also possible to employ one of the two components in a larger excess. The reaction is in general carried out in a suitable diluent, and the reaction mixture is stirred at the required temperature for several hours. In this process, working up is effected by customary methods.

In the preparation of optical isomers of the substituted alkanethiocarboxylic acid derivatives of the formula (I), the advantageous procedure is first to prepare the particular phenoxyalkanecarboxylic acid derivatives of the formula (IIa) on which the products are based by the method described in DE-OS (German Published Specification) No. 2,758,002 and then to convert these substances of the formula (IIa) into the corresponding thio compounds by the process according to the invention.

The active compounds according to the invention can be used as defoliants, desiccants, agents for destroying broad-leaved plants and especially as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium. Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusin, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers; optionally with the use of surface-active agents, that is, emulsifying agents and/or dispersing agents, and/or foamforming agents.

In the case of the use of water as an extender, organic solvents can, for example, also be used as auxiliary solvents. As liquid solvents, there are suitable in the main: aromatics, such as xylene, toluene, alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts, ground natural minerals, such as kaolins, clays, talc, chalk, quartz, attapulgite, montmorillonite or diatomaceous earth, and ground synthetic minerals, such as highly-dispersed silicic acid, alumina and silicates, as solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H-3H)-dione or N-(2-benzothiazolyl)-N,N'-dimethyl-urea, for combating weeds in cereals; 4-amino-3-methyl-6-phenyl-1,2,4-triazin-5(4H)-one, for combating weeds in sugar-beet, and 4-amino-6-(1,1-dimethylethyl)-3-methylthio-1,2,4-triazin-5(4H)-one for combating weeds in soya bean. Surprisingly, some mixtures also exhibit a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.01 and 5 kg/per ha.

The preparation and use of the active compounds according to the invention can be seen from the following examples.

PREPARATION EXAMPLES

EXAMPLE 1

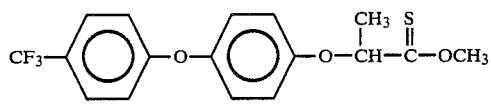

17 g (0.05 mol) of methyl 2-[4-(4-trifluoromethylphenoxy)-phenoxy]-propionate and 23.4 g (0.06 mol) of 2,4-bis(4-methoxyphenyl)-1,3,2,4-dicyclothiaphosphane-2,4-disulphide in 100 ml of xylene were heated under reflux for 28 hours. The solvent was then removed under a water pump vacuum, the residue was dissolved in hot ligroin and the solution was stirred with active charcoal. After hot filtration, the ligroin was then distilled off.

14.2 g (80% of theory) of methyl 2-[4-(4-trifluoromethyl)-phenoxy)-phenoxy]-thiopropionate were obtained.

The product was purified by chromatography over a silica gel column with an eluting agent of hexane and acetone=9:1.

$n_D^{21} = 1.5382$.

The substances listed by way of their formulae in the following Table 8 were also prepared by the method described in Example 1.

TABLE 8

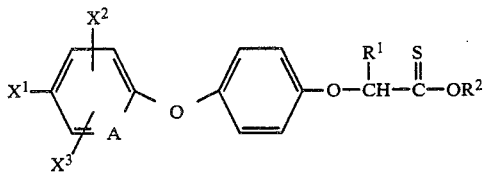

| Example No. | A | $X^1$ | $X^2$ | $X^3$ | $R^1$ | $R^2$ | Melting point or refractive index |
|---|---|---|---|---|---|---|---|
| 2 | —CH | Cl | 2-CF$_3$ | H | CH$_3$ | CH$_3$ | $n_D^{21}$: 1.5499 |
| 3 | —CH | H | 3-CF$_3$ | H | CH$_3$ | C$_2$H$_5$ | $n_D^{21}$: 1.5307 |
| 4 | —N | CF$_3$ | H | H | CH$_3$ | CH$_3$ | $n_D^{21.5}$: 1.5396 |
| 5 | —N | Cl | 2-Cl | H | CH$_3$ | CH$_3$ | $n_D^{21.5}$: 1.5966 |
| 6 | —CH | CF$_3$ | H | H | CH$_3$ | C$_2$H$_5$ | $n_D^{20.5}$: 1.5307 |
| 7 | —N | CF$_3$ | H | H | CH$_3$ | C$_2$H$_5$ | m.p.: 80° C. |
| 8 | —N | Cl | 2-Cl | H | CH$_3$ | C$_2$H$_5$ | $n_D^{20.5}$: 1.5824 |
| 9 | —CH | Cl | 2-Cl | H | CH$_3$ | CH$_3$ | $n_D^{21.5}$: 1.5925 |
| 10 | —N | CF$_3$ | 2-Cl | H | CH$_3$ | CH$_2$—CH$_2$—OC$_2$H$_5$ $n_D^{20}$ = 1.5229 |

The following compound was used as the comparison substance in the biological test described below:

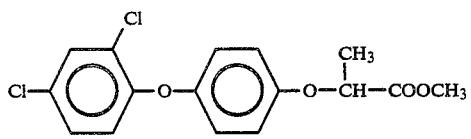

methyl 2-[4-(2,4-dichlorophenoxy)-phenoxy]-propionate (known from DE-OS (German Published Specification) 2,223,894).

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

The figures denote:

0% = no action (like untreated control)

100% = total destruction

In this test, active compounds (1), (4) and (5) according to the invention exhibit a better selective herbicidal activity than the comparison substance (A) in combating Alopecurus, Echinochloa and Setaria in sugar-beet when applied in an amount of 0.5 kg of active compound per hectare.

What is claimed is:

1. A substituted alkanethiocarboxylic acid derivative of the formula in which

A represents a —CH-grouping, $X^1$ represents hydrogen, trifluoromethyl or chlorine, $X^2$ represents hydrogen, trifluoromethyl or chlorine, $X^3$ represents hydrogen, trifluoromethyl or chlorine, $R^1$ represents hydrogen or methyl and $R^2$ represents hydrogen, or represents alkyl which has 1 to 6 carbon atoms and is optionally substituted by hydroxyl, halogen, C$_1$–C$_4$-alkoxy, C$_1$–C$_4$-alkylthio, C$_3$–C$_6$-cycloalkyl, amino, alkylamino with 1 to 4 carbon atoms, dialkylamino with 1 to 4 carbon atoms per alkyl radical and/or saturated 5-membered or 6-membered heterocyclic radicals which are bonded via nitrogen and contain up to 3 nitrogen and/or oxygen atoms, or represents alkenyl which is optionally substituted by fluorine, chlorine, bromine and/or iodine, or represents alkinyl which is optionally substituted by fluorine, chlorine, bromine and/or iodine, or represents phenyl which is optionally substituted by halogen, C$_1$–C$_4$-alkyl, C$_1$–C$_4$-alkythio, C$_1$–C$_4$-alkoxy, cyano and/or nitro, or represents benzyl which is optionally substituted by halogen, C$_1$–C$_4$-alkylthio, C$_1$–C$_4$-alkoxy, cyano and/or nitro, or represents phenethyl which is optionally substituted in the phenyl part by halogen, $C_1$-$C_4$-alkyl, $C_1$-$C_4$-alkylthio, $C_1$-$C_4$-alkoxy, cyano and/or nitro, or represents phenyl-($C_1$-$C_4$)-alkoxy-($C_1$-$C_4$)-alkyl which is optionally substituted in the phenyl part by halogen, $C_1$-$C_4$-alkyl, $C_1$-$C_4$-alkylthio, $C_1$-$C_4$-alkoxy, cyano and/or nitro, or represents cycloalkyl which has 3 to 6 carbon atoms and is optionally substituted by alkyl with 1 to 4 atoms and/or halogen.

2. A substituted alkanethiocarboxylic acid derivative according to claim 1 wherein $R^2$ is alkyl.

3. A substituted alkanethiocarboxylic acid according to claim 2 wherein $R^1$ is hydrogen or methyl.

4. A substituted alkanethiocarboxylic acid according to claim 3, wherein $X^1$ is hydrogen, trifluoromethyl or chloro.

5. A substituted alkanethiocarboxylic acid according to claim 4, wherein $X^3$ is hydrogen.

6. A substituted alkanethiocarboxylic acid according to claim 5, wherein $X^2$ is 2—$CF_3$, 3—$CF_3$, H or 2—Cl.

7. A compound according to claim 6, wherein A is a CH grouping.

8. A compound according to claim 1, wherein A is a CH grouping.

9. A compound according to claim 1 of the formula

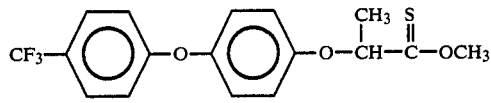

10. A herbicidal composition comprising a herbicidally effective amount of a substituted alkanethiocarboxylic acid according to claim 1 and a diluent.

11. A composition according to claim 10 wherein said substituted alkanethiocarboxylic acid is present in said composition in an amount of 0.01 to 95% by weight, based upon the weight of said composition.

12. A composition according to claim 11, wherein said substituted alkanethiocarboxylic acid compound is present in an amount of 0.5 to 90% by weight based upon the weight of the said composition.

13. A process for combating weeds which comprises applying to the weeds or their habitat a substantial alkanethiocarboxylic acid derivative according to claim 1 in a herbicidally effective amount.

14. A process according to claim 13, wherein said substituted alkanethiocarboxylic acid derivatives is applied in an amount of 0.001 and 10 kg/per hectare of soil surface.

15. A process according to claim 14, wherein said substituted alkanethiocarboxylic acid derivative is applied to said weeds after emergence thereof.

* * * * *

UNITED STATES PATENT AND TRADEMARK OFFICE
CERTIFICATE OF CORRECTION

PATENT NO. : 4,599,106

DATED : July 8, 1986

INVENTOR(S) : Heinz Förster, et al.

It is certified that error appears in the above-identified patent and that said Letters Patent is hereby corrected as shown below:

Col. 3, Table 1, lines 6, 7, 8 and 9 under "$R^2$" first instance and line 2 under "$R^2$" second instance — Delete "$CH_3$" and substitute --$CH_2$--

Col. 9, line 14 — Correct "Lycopersicon"

Col. 13, line 10 — After "1 to 4" insert --carbon--

Col. 14, line 19 — Delete "substantial" and substitute --substituted--

Signed and Sealed this

Twenty-first Day of October, 1986

[SEAL]

Attest:

DONALD J. QUIGG

Attesting Officer

Commissioner of Patents and Trademarks